(12) United States Patent
Rioux et al.

(10) Patent No.: US 8,795,272 B2
(45) Date of Patent: Aug. 5, 2014

(54) LIQUID DELIVERY APPARATUS FOR TISSUE ABLATION

(75) Inventors: Robert Rioux, Ashland, MA (US); Jeffrey Bean, Fitchburg, MA (US)

(73) Assignee: Bovie Medical Corporation, Clearwater, FL (US)

( * ) Notice: Subject to any disclaimer, the term of this patent is extended or adjusted under 35 U.S.C. 154(b) by 914 days.

(21) Appl. No.: 12/959,792

(22) Filed: Dec. 3, 2010

(65) Prior Publication Data

US 2011/0077640 A1      Mar. 31, 2011

Related U.S. Application Data

(63) Continuation of application No. 11/323,600, filed on Dec. 29, 2005, now abandoned.

(51) Int. Cl.
*A61B 18/14* (2006.01)

(52) U.S. Cl.
USPC .................................. 606/45; 606/41; 606/49

(58) Field of Classification Search
USPC .......................................... 606/37–41, 45–50
See application file for complete search history.

(56) References Cited

U.S. PATENT DOCUMENTS

| | | | | |
|---|---|---|---|---|
| 5,019,038 A | * | 5/1991 | Linden | 604/540 |
| 5,085,657 A | * | 2/1992 | Ben-Simhon | 606/42 |
| 5,167,659 A | | 12/1992 | Ohtomo et al. | |
| 5,224,944 A | * | 7/1993 | Elliott | 606/41 |
| 5,230,704 A | | 7/1993 | Moberg et al. | |
| 5,254,117 A | | 10/1993 | Rigby et al. | |
| 5,273,524 A | | 12/1993 | Fox et al. | |
| 5,429,596 A | | 7/1995 | Arias et al. | |
| 5,609,573 A | | 3/1997 | Sandock | |
| 5,674,219 A | * | 10/1997 | Monson et al. | 606/45 |
| 5,836,909 A | | 11/1998 | Cosmescu | |

(Continued)

FOREIGN PATENT DOCUMENTS

| | | |
|---|---|---|
| EP | 0684015 A1 | 11/1995 |
| EP | 0895756 A1 | 10/1999 |

(Continued)

OTHER PUBLICATIONS

European Search Report for European Application No. 12153879.7; dated Aug. 2, 2012; five (5) pages.

(Continued)

*Primary Examiner* — Michael Peffley
(74) *Attorney, Agent, or Firm* — Michael J. Porco; Gerald E. Hespos; Matthew T. Hespos

(57) ABSTRACT

An apparatus for use in a tissue ablation procedure includes a base, a fluid delivery tube coupled to the base, a first lever rotatably coupled to the base, the first lever having a first end biased to press against a portion of the fluid delivery tube to thereby close a lumen within the fluid delivery tube, and a second end, and a securing mechanism for securing the base relative to an ablation device. An ablation system includes an ablation device having an electrode, a fluid delivery tube coupled to the ablation device, and a control for simultaneously activating the electrode and opening the fluid delivery tube. A method of performing tissue ablation includes operating a control to activate an electrode, thereby delivering ablation energy to target tissue, wherein the step of operating the control also causes fluid to be delivered to the target tissue.

23 Claims, 8 Drawing Sheets

(56) References Cited

U.S. PATENT DOCUMENTS

| | | | |
|---|---|---|---|
| 5,897,553 | A | 4/1999 | Mulier et al. |
| 5,989,211 | A | 11/1999 | Schaumann et al. |
| 6,050,992 | A | 4/2000 | Nichols |
| 6,212,433 | B1 | 4/2001 | Behl |
| 6,235,022 | B1 | 5/2001 | Hallock et al. |
| 6,355,034 | B2 | 3/2002 | Cosmescu |
| 6,635,034 | B1 | 10/2003 | Cosmescu |
| 6,716,211 | B2 | 4/2004 | Mulier et al. |
| 7,083,601 | B1 * | 8/2006 | Cosmescu ............ 604/289 |
| 7,621,911 | B2 * | 11/2009 | Ariola, Jr. ............ 606/51 |
| 2002/0026187 | A1 | 2/2002 | Swanson |
| 2003/0009164 | A1 | 1/2003 | Woloszko et al. |
| 2003/0216724 | A1 | 11/2003 | Jahns |
| 2005/0171528 | A1 | 8/2005 | Sartor et al. |

FOREIGN PATENT DOCUMENTS

| | | |
|---|---|---|
| GB | 2188845 | 10/1987 |
| GB | 2352797 A | 2/2001 |
| WO | 96/29946 A1 | 10/1996 |
| WO | 00/35530 A1 | 6/2000 |
| WO | 02/089686 A1 | 11/2002 |
| WO | 03/082134 A1 | 10/2003 |

OTHER PUBLICATIONS

PCT International Search Report dated Nov. 21, 2007 for related International Application Serial No. PCT/US2006/062110 filed Dec. 14, 2006.

PCT Written Opinion dated Nov. 21, 2007 for related International Application Serial No. PCT/US2006062110 filed Dec. 14, 2006.

Office Action issued by European Patent Office on Aug. 9, 2011 regarding corresponding European Application No. 06849058.0.

* cited by examiner

LIQUID DELIVERY APPARATUS FOR TISSUE ABLATION

CLAIM OF PRIORITY

This application is a continuation of U.S. patent application Ser. No. 11/323,600, filed on Dec. 29, 2005, now abandoned, the entire disclosure of which is incorporated by reference herein.

FIELD

The field of the application relates to apparatus for delivery of fluids for enhancing thermal heating and ablation of the tissue.

BACKGROUND

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction.

In particular, radio frequency ablation (RFA) may be used to treat patients with tissue anomalies, such as liver anomalies and many primary cancers, such as cancers of the stomach, bowel, pancreas, kidney and lung. RFA treatment involves the destroying undesirable cells by generating heat through agitation caused by the application of alternating electrical current (radio frequency energy) through the tissue.

Various electrosurgical instruments have been suggested for this purpose. For example, published PCT application WO 96/29946 discloses electrosurgical probes that include a number of independent wire electrodes that may be extended into tissue from the distal end of a cannula. The electrodes may be energized in a monopolar or bipolar manner to heat and necrose a target tissue region. Such probes have been suggested for treating tumors within organs, such as the liver, kidney, pancreas, stomach, and spleen.

To enhance heating and necrosis, saline may be injected into the target region before delivering electrical energy. Generally, this involves advancing a needle from a syringe into the tissue before or after advancing the electrodes from an electrosurgical probe into the target region. Saline may be delivered from the syringe into the tissue through the needle, and then the electrodes may be energized to deliver RF energy and necrose tissue within the target region. Alternatively, saline may be delivered through a lumen in one or more of the wire electrodes. Saline may increase heating of the tissue, thereby increasing the size of the resulting lesion, as compared to energizing the electrodes without saline.

In existing ablation devices that have fluid delivery capability, the activation of the ablation electrode is controlled by a first control, such as a button, and the delivery of the fluid is controlled by a second control, such as a plunger. However, such device is cumbersome to use because it requires a physician to perform two separates steps, i.e., a first step to operate the ablation device, and a second step to operate the fluid delivery mechanism.

In addition, some existing ablation devices do not have a fluid delivery capability. In such cases, a physician will have to find another device for delivering saline. For example, the physician may use a separate syringe for delivering saline. However, where a separate syringe is used to deliver the saline, the syringe and the ablation device require separate handling by the physician, thereby complicating the procedure.

SUMMARY

In accordance with some embodiments, an apparatus for use in a tissue ablation procedure includes a base, a fluid delivery tube coupled to the base, a first lever rotatably coupled to the base, the first lever having a first end biased to press against a portion of the fluid delivery tube to thereby close a lumen within the fluid delivery tube, and a second end, and a securing mechanism for securing the base relative to an ablation device.

In accordance with other embodiments, an ablation system includes an ablation device having an electrode, a fluid delivery tube coupled to the ablation device, and a control for simultaneously activating the electrode and opening the fluid delivery tube.

In accordance with other embodiments, a method of performing tissue ablation includes operating a control to activate an electrode, thereby delivering ablation energy to target tissue, wherein the step of operating the control also causes fluid to be delivered to the target tissue.

Other aspects and features of the embodiments will be evident from reading the following description of the embodiments.

BRIEF DESCRIPTION OF THE DRAWINGS

The drawings illustrate the design and utility of embodiments of the application, in which similar elements are referred to by common reference numerals. In order to better appreciate how advantages and objects of various embodiments are obtained, a more particular description of the embodiments are illustrated in the accompanying drawings. Understanding that these drawings depict only typical embodiments of the application and are not therefore to be considered limiting its scope, the embodiments will be described and explained with additional specificity and detail through the use of the accompanying drawings.

DESCRIPTION OF THE EMBODIMENTS

Figure 1A:
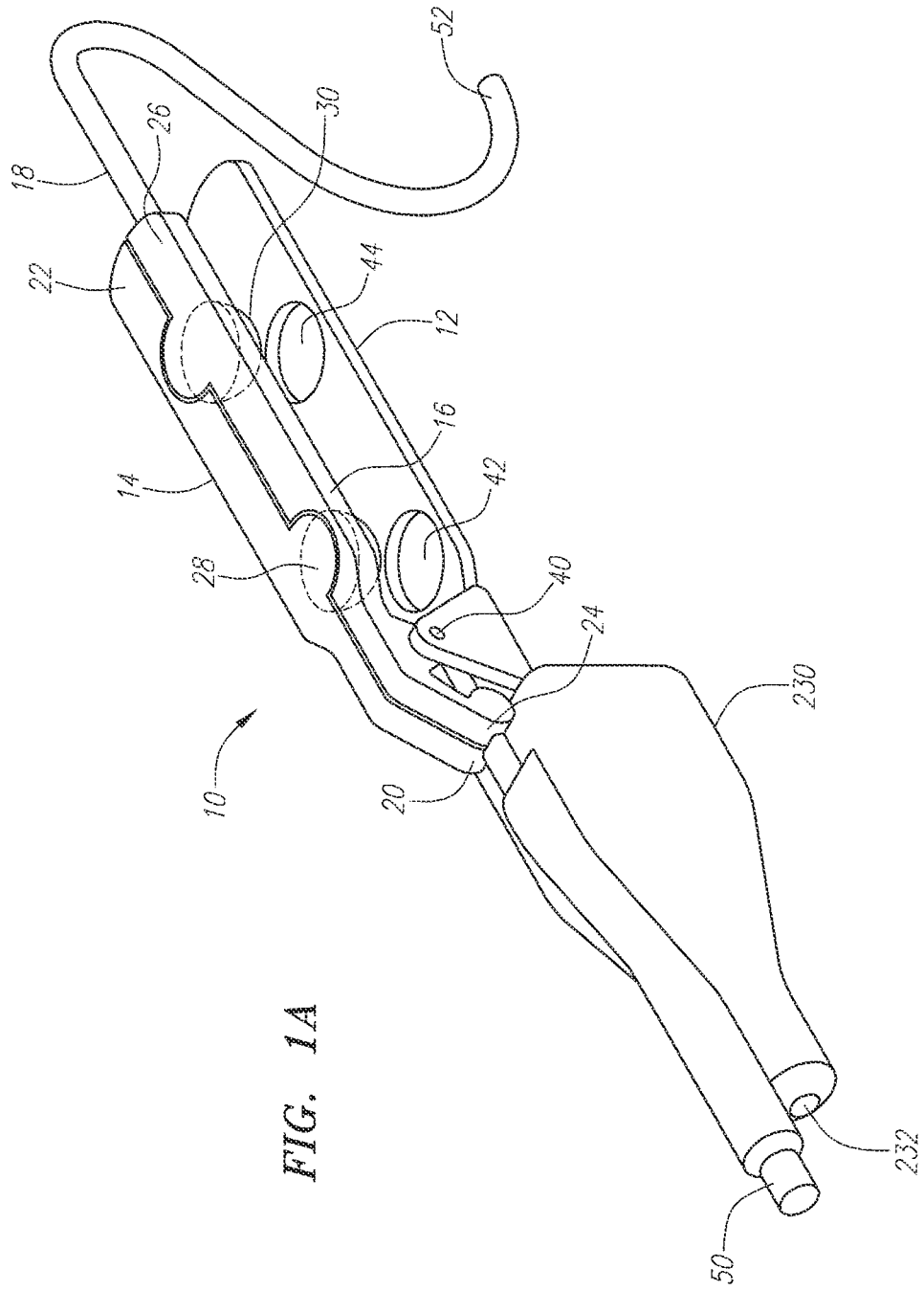
FIG. 1A illustrates a fluid delivery apparatus in accordance with some embodiments.

Various embodiments are described hereinafter with reference to the figures. It should be noted that the figures are not drawn to scale and elements of similar structures or functions are represented by like reference numerals throughout the figures. An aspect, a feature, or an advantage described in conjunction with a particular embodiment is not necessarily limited to that embodiment and can be practiced in any other embodiments described herein.

FIG. 1A illustrates a fluid delivery apparatus 10 configured to be used with an ablation device in accordance with some embodiments. The apparatus 10 has a base 12, a first lever 14, a second lever 16, and a fluid delivery tube 18. In the illustrated embodiments, the base 12 has a planar configuration. However, the base 12 can have other configurations in other embodiments. It should be noted that the word "base", as used in this specification, refers to a structure to which other components of the apparatus 10, such as the lever 14 or the tube 18 may be coupled. As such, the base 12 needs not be in any particular position relative to other components of the apparatus 10. For example, the base 12 needs not be located at a bottom of the apparatus 10.

The first lever 14 has a first end 20 for pressing against a portion of the fluid delivery tube 18, and a second end 22. Similarly, the second lever 16 has a first end 24 for pressing against a portion of the fluid delivery tube 18, and a second end 26. The first and the second levers 14, 16 are rotatably coupled to the base 18 via a shaft 40. The fluid delivery tube 18 has a distal end 50 and a proximal end 52, which connects to a fluid source, such as a bag of saline, a source of conductive fluid, or other fluid sources.

Figure 2:
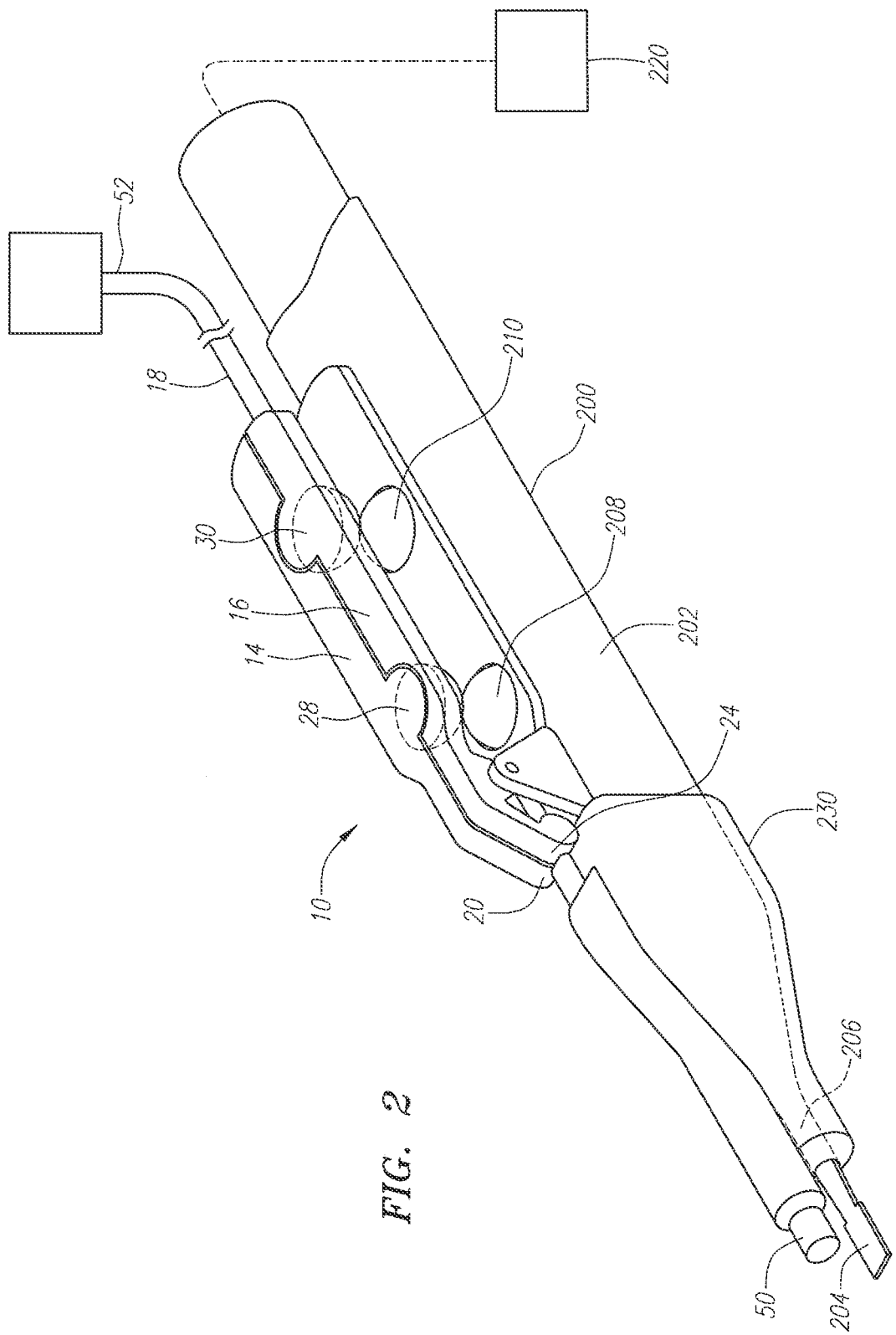
FIG. 2 illustrates the fluid delivery apparatus of FIG. 1A, showing the apparatus being secured to an ablation device in accordance with some embodiments.

FIG. 2 illustrates the fluid delivery apparatus 10 being used with an ablation device 200 in accordance with some embodiments. The ablation device 200 includes a probe 202, an electrode 204 located at a distal end 206 of the probe 202, a first switch 208, and a second switch 210. The ablation device 200 may be any device that is configured to deliver energy to heat tissue. For example, the ablation device 200 can be a cautery pen. During use, the ablation device 200 is electrically coupled to a generator 220, e.g., a radio frequency (RF) generator, which delivers energy to the electrode 204. In some embodiments, the first switch 208 is configured such that when it is pressed, the electrode 204 will be activated to deliver energy at a first energy level, and the second switch 210 is configured such that when it is pressed, the electrode 204 will be activated to deliver energy a second energy level. For example, the first energy level may be that which is suitable for cutting tissue, and the second energy level may be that which is suitable for coagulating target area.

In the illustrated embodiments, the apparatus 10 includes a sleeve 230 that fits over the distal end 206 of the ablation device 200, thereby securing the apparatus 10 relative to the ablation device 200. The sleeve 230 includes a distal opening 232 for allowing a portion of the ablation device 200 to exit therethrough. As shown in the figure, the sleeve 230 has a shape that resembles a nosecone. In other embodiments, the sleeve 230 can have other shapes and configurations, depending on the configuration of the ablation device 200 to which the apparatus 10 is secured. When the fluid delivery apparatus 10 is secured to the ablation device 200, the distal end 50 of the tube 18 is located next to the electrode 204.

It should be noted that the manner in which the fluid delivery apparatus 10 is secured to the ablation device 200 is not limited to the example described previously, and that the fluid delivery apparatus 10 can have other securing mechanisms for securing to the ablation device 200 in other embodiments. For example, in other embodiments, the fluid delivery apparatus 10 can include a strap that ties around a circumference of the ablation device 200, a snap-on that mates with a portion of the ablation device 200, a tongue that mates with a groove on the ablation device 200, or a double-sided adhesive tape, for securing itself to the ablation device 200. In further embodiments, instead of having a securing mechanism that allows the fluid delivery apparatus 10 to be detachably secured to the ablation device 200, the securing mechanism can be used to permanently secure the fluid delivery apparatus 10 to the ablation device 200. For example, in other embodiments, the fluid delivery apparatus 10 further includes a glue that can be applied between the fluid delivery apparatus 10 and the ablation device 200, thereby permanently securing the fluid delivery apparatus 10 to the ablation device 200.

Figure 1B:
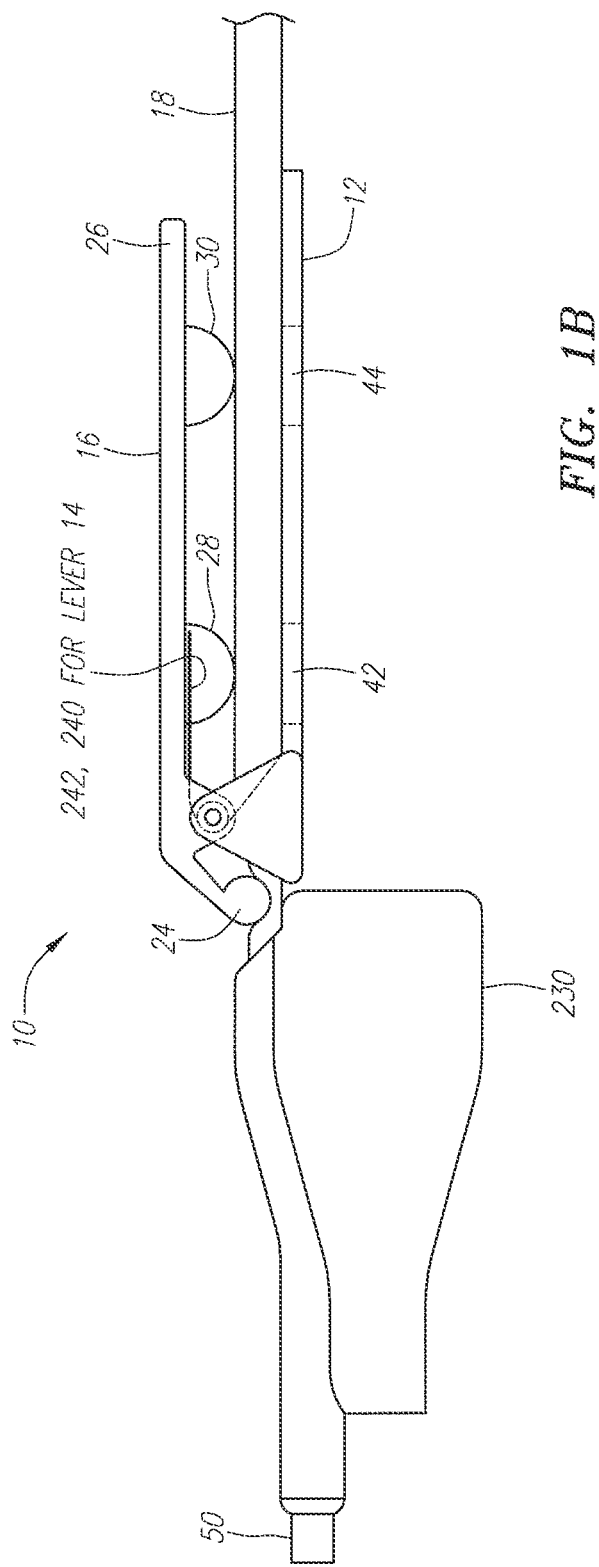
FIG. 1B is a side view of the fluid delivery apparatus of FIG. 1A.

As shown in FIGS. 1 and 2, the base 12 includes a first opening 42 and a second opening 44 that correspond with the locations of the first and second switches 208, 210, respectively, of the ablation device 200. As such, when the fluid delivery apparatus 10 is secured to the ablation device 200, the first and the second switches 208, 210 extend at least partially into the first and the second openings 42, 44, respectively. The first lever 14 has a portion 28 for engaging with the first switch 208, and the second lever 16 has a portion 30 for engaging with the second switch 210. In the illustrated embodiments, the portions 28, 30 are each in a form of a protrusion that extends from a surface of the levers 14,16, respectively. In other embodiments, the portions 28, 30 can have other configurations.

Figure 3:
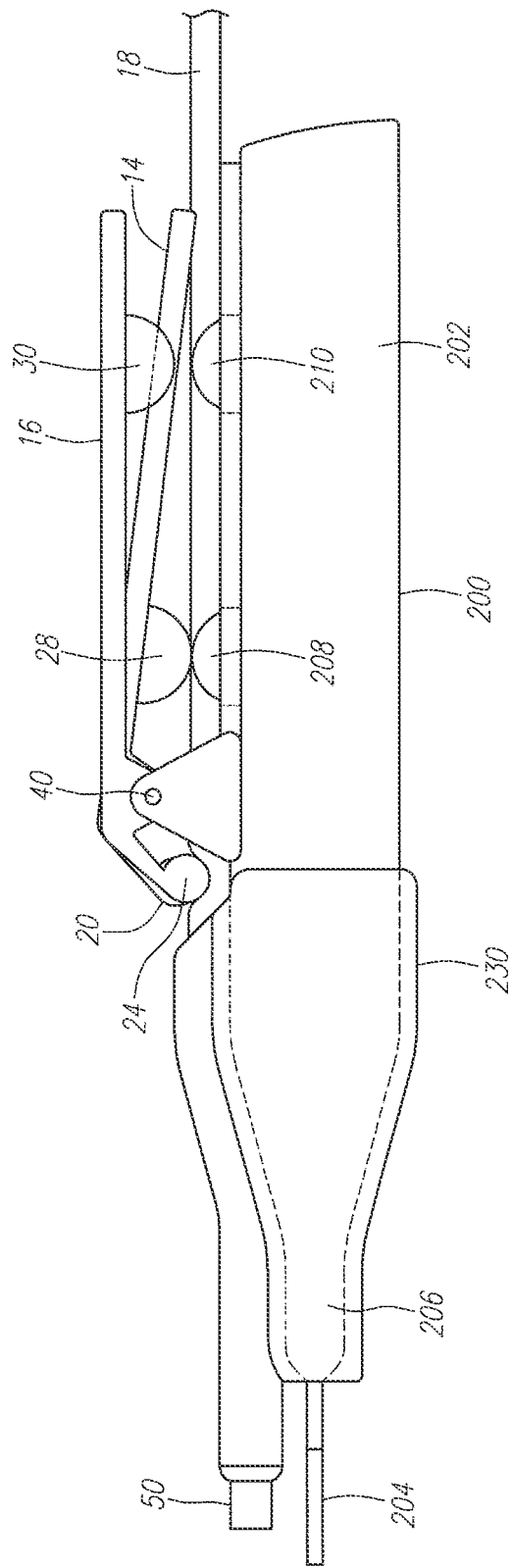
FIG. 3 illustrates the fluid delivery apparatus of FIG. 1A, showing a first lever being pressed.
Figure 4:
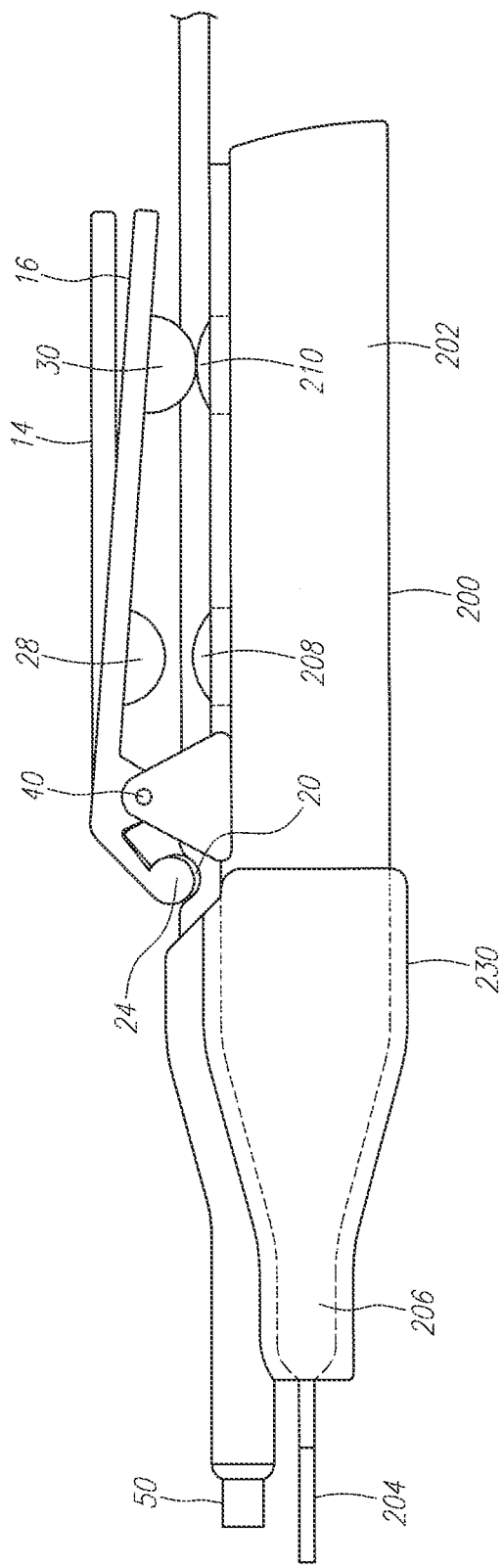
FIG. 4 illustrates the fluid delivery apparatus of FIG. 1A, showing a second lever being pressed.

In the illustrated embodiments, the levers 14, 16 are biased by springs 240, 242, respectively, such that the respective first ends 20, 24 are pressed against portions of the fluid delivery tube 18. The levers 14, 16 are located relative to each other in a side-by-side manner such that the first end 20 of the first lever 14 presses against half of a cross section of the tube 18, and the first end 24 of the second lever 16 presses against the other half of the cross section of the tube 18. Such configuration allows the first end 20 to be moved apart from the tube 18 to partially open the lumen of the tube 18, when the second end 22 of the first lever 14 is pressed towards the base 12 to engage the first switch 208 (FIG. 3). Such configuration also allows the first end 24 to be moved apart from the tube 18 to partially open the lumen of the tube 18, when the second end 26 of the second lever 16 is pressed towards the base 12 to engage the second switch 210 (FIG. 4).

During use, a user can selectively press either the first lever 14 or the second lever 16 to active the first switch 208 or the second switch 210, respectively. For example, during a procedure, if a physician wishes to cut tissue, the physician can press the second end 22 of the first lever 14 towards the base 12 until the portion 28 contacts and presses the first switch 208. This in turn, activates the electrode 204 to deliver energy for cutting tissue, and at the same time, opens the tube 18 to allow fluid, such as saline, to be delivered to the electrode 204. In some cases, the fluid source 220 may be placed at an elevation that is higher than the fluid delivery apparatus 10, thereby allowing fluid to be delivered by pressure induced under gravitational force. Alternatively, the fluid source 220 may be coupled to a pump for delivering fluid. The delivered saline may couple electrical energy to tissue. In some cases, the delivered saline also shrinks collagen, closes vessels, and stops bleeding at the target tissue which has been cut. The saline may also keep the electrode 204 surface cool (e.g., 100. degree. C. or below). In some embodiments, the fluid delivery apparatus 10 is configured (e.g., by selecting an appropriate height for the protrusion 28) such that the fluid delivery tube 18 will open just prior to the protrusion 28 depressing the first switch 208. When the first lever 14 is released, the first lever 14 will spring back to its initial position (due to the spring 240), thereby clamping the lumen of the tube 18 closed and stopping the flow of saline.

Alternatively if a physician wishes to coagulate a target tissue, the physician can press the second end 22 of the second lever 16 towards the base 12 until the portion 30 contacts and presses the second switch 210. This in turn, activates the electrode 204 to deliver energy for tissue coagulation, and at the same time, opens the tube 18 to allow fluid, such as saline, to be delivered to the electrode 204. The delivered saline may couple electrical energy to tissue. The saline may also keep the electrode 204 surface cool. In some embodiments, the fluid delivery apparatus 10 is configured (e.g., by selecting an appropriate height for the protrusion 30) such that the fluid delivery tube 18 will open just prior to the protrusion 30 depressing the switch 210. When the second lever 16 is released, the second lever 16 will spring back to its initial position (due to the spring 242), thereby clamping the lumen of the tube 18 closed and stopping the flow of saline.

As shown in the above embodiments, the fluid delivery apparatus 10 is advantageous in that it allows a physician to activate the electrode 204 and cause delivery of fluid by the use of one finger in a single step. As a result, the physician does not need to manipulate multiple controls (e.g., one for ablation, and another for fluid delivery), or to handle multiple instruments (e.g., ablation device and syringe) during the ablation process.

Figure 5:
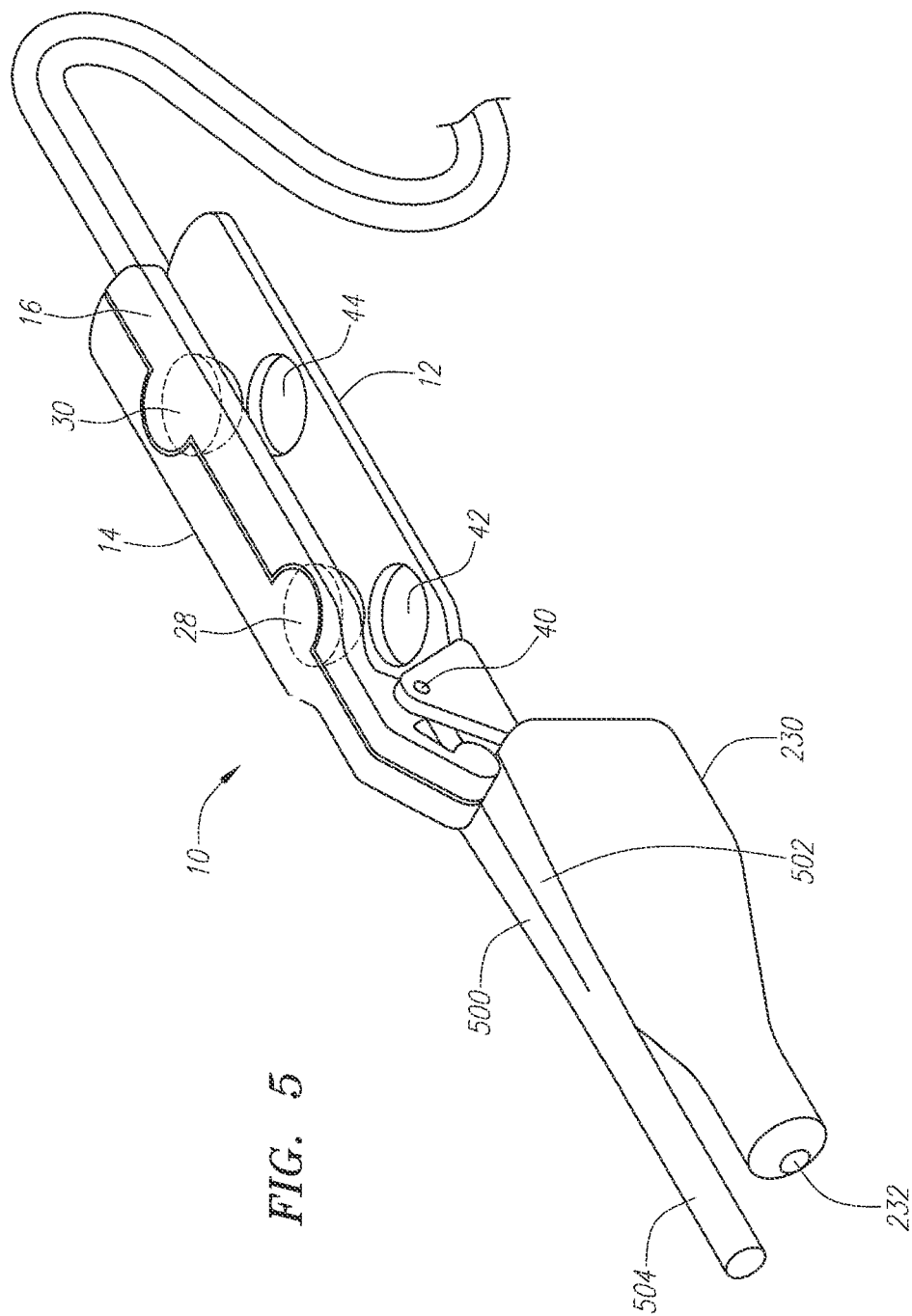
FIG. 5 illustrates a fluid delivery apparatus in accordance with other embodiments.

In the above embodiments, the first end 20 of the first lever 14 presses against half of the delivery tube 18 and the first end 24 of the second lever 16 presses against the other half of the delivery tube 18. Alternatively, the apparatus 20 can have two fluid delivery tubes 500, 502 (FIG. 5). In such cases, the first end 20 of the first lever 14 presses against the delivery tube 500, and the first end 24 of the second lever 16 presses against the delivery tube 502. In the illustrated embodiments, the delivery tubes 500, 502 join into a distal tube 504. During use, when the first lever 14 is pressed to engage the first switch 208 on the ablation device 200, the first end 20 is moved apart from the first delivery tube 500, thereby creating an unobstructed flow of fluid through the tube 500 and allowing fluid to be delivered through the tube 500 and into the tube 504. The fluid exits from the distal end of the tube 504 and onto the electrode 204. Similarly, when the second lever 16 is pressed to engage the second switch 210 on the ablation device 200, the first end 24 is moved apart from the second delivery tube 502, thereby creating an unobstructed flow of fluid through the tube 502 and allowing fluid to deliver through the tube 502 and into the tube 504. The fluid exits from the distal end of the tube 504 and onto the electrode 204.

Figure 6:
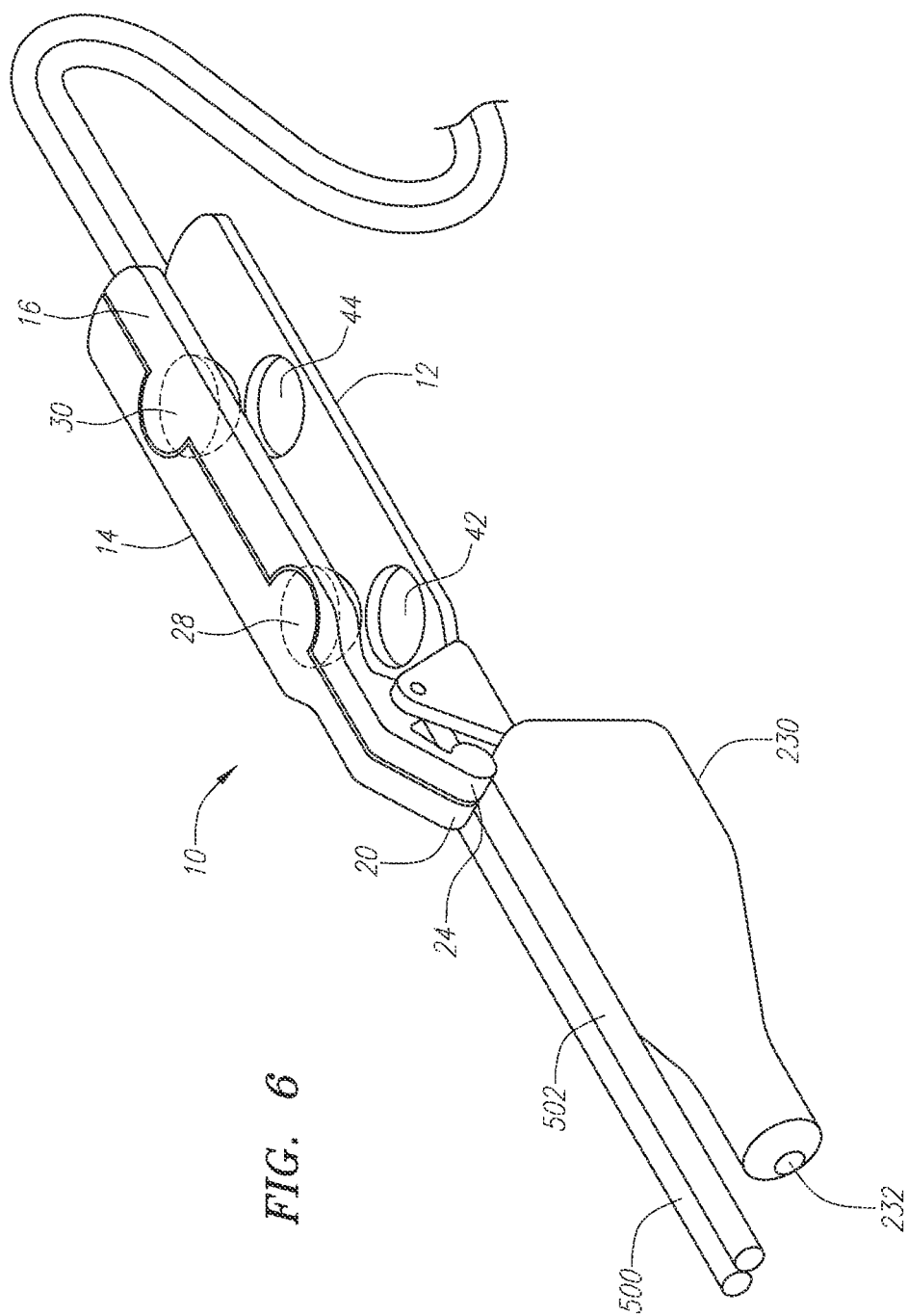
FIG. 6 illustrates a fluid delivery apparatus in accordance with other embodiments.

In further embodiments, the apparatus 10 does not include the distal tube 504 (FIG. 6). In such cases, the fluid exits from the distal end of the tube 500 or the tube 502, and onto the electrode 204.

In the above embodiments, the fluid delivery apparatus 10 has been described as having two levers 14, 16. In other embodiments, the fluid delivery apparatus 10 can have other numbers of levers. For example, the fluid delivery apparatus 10 can have one lever for engaging with one button, or more than two levers for engaging with more than two switches, on an ablation device.

Figure 7:
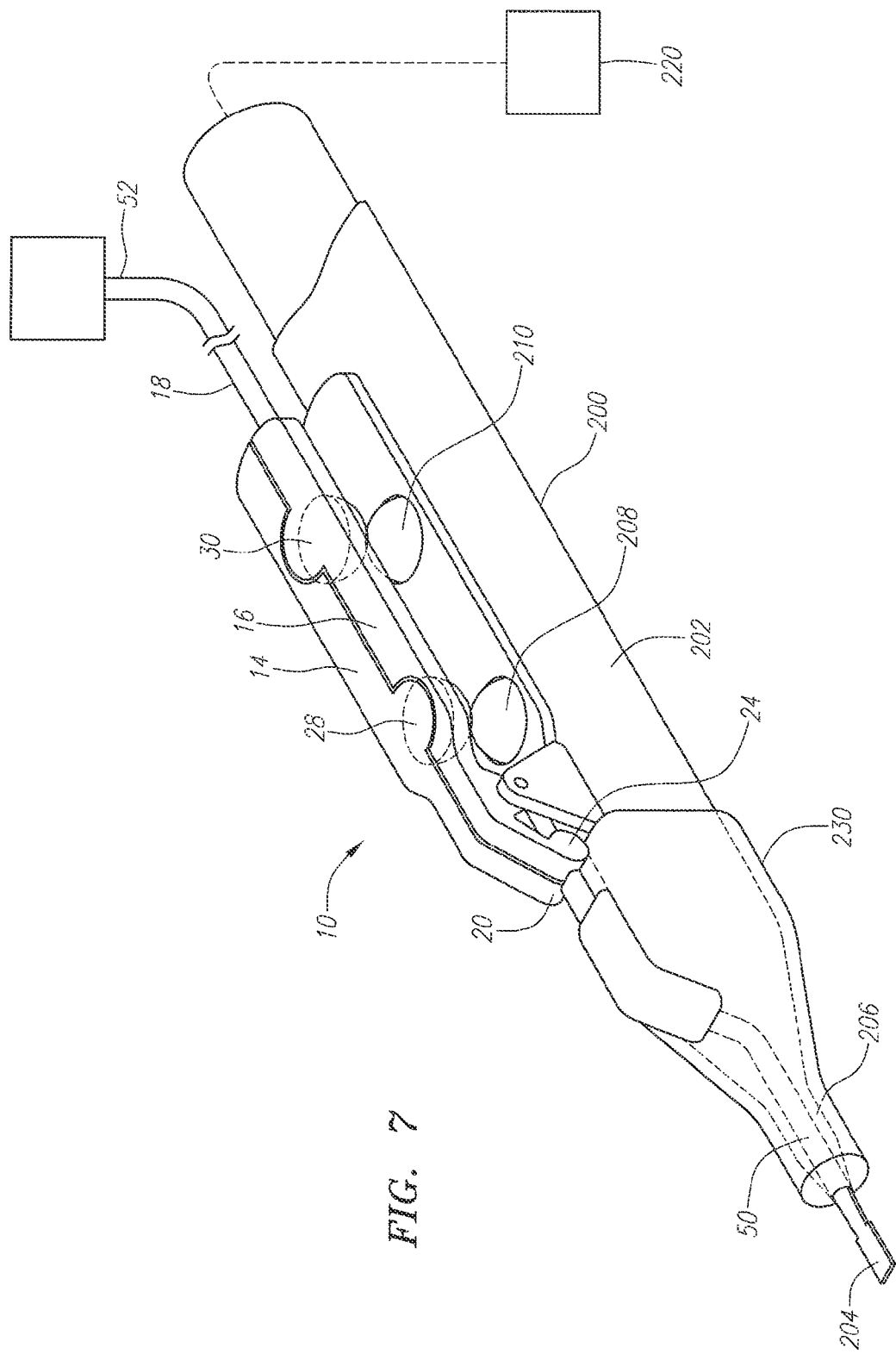
FIG. 7 illustrates an ablation device having a fluid delivery apparatus in accordance with other embodiments.

Also, in the above embodiments, the fluid delivery apparatus 10 has been described as having delivery tube(s) that deliver fluid from external of the electrode 204. In other embodiments, the delivery tube described herein can be at least partially placed within the ablation device 200 to thereby allow fluid to be delivered from within the electrode 204 (FIG. 7). In such cases, the electrode 204 will have a plurality of openings or pores for allowing fluid delivered from the tube(s) to exit therethrough. For example, the electrode 204 can have a sintered configuration (e.g., made from a plurality of particles connected together).

In further embodiments, the fluid delivery apparatus 10 can be built within the ablation device 200 itself. For example, the first lever 14 can be placed underneath the switch 208, and the second lever 16 can be placed underneath the second switch 210. In other embodiments, instead of, or in addition to, implementing the fluid delivery apparatus 10 using mechanical components, the apparatus 10 can be implemented using electrical components.

For example, in some embodiments, the first switch 208 is electrically coupled to a first positioner, which pushes a block against, or removes the block from, at least a portion of the tube 18. The first switch 208 is also coupled to the electrode 204 such that when the first switch 208 is pressed, the electrode 204 will be activated to delivery energy at a first energy level, and the block will move apart from the tube 18 to allow fluid to be delivered via the tube 18. When the first switch 208 is released, the electrode 204 will stop delivering energy, and the positioner will move the block towards the tube 18 to press against the tube 18, thereby stopping flow of fluid within the tube 18.

Similarly, the second switch 210 is electrically coupled to a positioner (which may be the same positioner associated with the first switch 208), which pushes a block against, or removes the block from, at least a portion of the tube 18. The second switch 210 is also coupled to the electrode 204 such that when the second switch 210 is pressed, the electrode 204 will be activated to deliver energy at a second energy level, and the block will move apart from the tube 18 to allow fluid to be delivered via the tube 18. When the second switch 210 is released, the electrode 204 will stop delivering energy, and the positioner will move the block towards the tube 18 to press against the tube 18, thereby stopping flow of fluid within the tube 18.

It should also be noted that the ablation device 200 with which the fluid delivery apparatus 10 can be used is not necessarily limited to the configurations described previously, and that the ablation device 200 can have other configurations in other embodiments. For example, in other embodiments, the ablation device 200 can have different shapes and/or sizes. Also, in other embodiments, instead of having one electrode 204 for delivering energy, the ablation device 200 can include a plurality of electrodes at the distal end of the probe 202. Further, instead of delivering heat energy, the ablation device 200 can delivery other forms of energy in other embodiments. For example, in other embodiments, the electrode 204 can be configured to deliver electrical energy. In further embodiments, the ablation device 200 can include one or more ultrasound transducers (for generating ultrasound energy), or one or more microwave energy generators (for generating microwave energy).

Thus, although several embodiments have been shown and described, it would be apparent to those skilled in the art that many changes and modifications may be made thereunto without the departing from the scope of the invention, which is defined by the following claims and their equivalents.

What is claimed:

1. A method of retrofitting a fluid delivery system to an electrosurgical device, the method comprising the steps of:
    a. providing a fluid delivery system having a base, a fluid delivery tube operatively connected to said base and a first lever having a first end and a second end, wherein said first lever is operatively coupled to said base; and
    b. securing said fluid delivery system base to an outer housing of the electrosurgical device such that said fluid delivery tube delivers fluid proximate a portion of the electrosurgical device, the portion used for delivering energy to tissue,
        wherein said first lever is configured to simultaneously activate the delivery of fluid proximate the electrosurgical device portion when said first lever first end moves out of engagement with said fluid delivery tube and to activate delivery of electrosurgical energy when said first lever second end engages an energy delivery switch of the electrosurgical device.

2. The method of claim 1, wherein the electrosurgical device is a radio frequency (RF) ablation device.

3. The method of claim 1, further comprising the step of biasing said first lever first end against a portion of said fluid delivery tube to close a lumen defined by said fluid delivery tube to prevent fluid from passing through said fluid delivery tube.

4. The method of claim 1, wherein said fluid is a conductive liquid.

5. The method of claim 1, wherein activation of the electrosurgical device and opening a lumen defined by said fluid delivery tube occur when said lever is pressed.

6. The method of claim 5, wherein fluid is simultaneously delivered proximate the electrosurgical device portion when said lever is pressed.

7. The method of claim 1, further comprising the step of providing a fluid source that is operatively coupled to said fluid delivery tube lumen.

8. The method of claim 7, wherein fluid from said fluid source is gravity fed through said fluid delivery tube.

9. The method of claim 1, wherein said fluid delivery system is disposable.

10. A method of attaching a fluid delivery system to an electrosurgical device, the method comprising the steps of
  a. providing a fluid delivery system having
    i. a fluid delivery tube having a first end operatively coupled to a fluid source, a second end for dispensing fluid and a lumen that extends between said first and said second ends, and
    ii. at least one lever in operative engagement with said fluid delivery tube and a power switch on the electrosurgical device,
  b. securing said fluid delivery tube and said at least one lever to the electrosurgical device external surface so that said fluid delivery tube second end is positioned proximate a working end of the electrosurgical device and said lever is positioned adjacent the power switch, wherein said first lever is biased into engagement with said fluid delivery tube to prevent dispensing of fluid from said fluid delivery tube second end.

11. The method of claim 10, wherein when said at least lever is pressed, fluid is dispensed from said fluid delivery tube second end while activating the electrosurgical device working end.

12. The method of claim 11, wherein
  a. said fluid delivery system further comprises a base that is configured to be removably attached to the electrosurgical device;
  b. said fluid delivery tube is operatively connected to said base; and
  c. said at least one lever is operatively coupled to said base and to the electrosurgical device power switch.

13. The method of claim 10, wherein a spring biases said at least one lever into engagement with said fluid delivery tube.

14. The method of claim 12, wherein a spring biases said lever into engagement with said fluid delivery tube and out of engagement with the electrosurgical device power switch.

15. The method of claim 10, wherein fluid in said fluid source is conductive.

16. The method of claim 10, wherein said fluid delivery system is disposable.

17. A method of attaching a fluid delivery system to an electrosurgical device, the method comprising the steps of:
  a. providing a fluid delivery system having
    i. at least one fluid tube having a first end operatively coupled to a fluid source and a second end for dispensing fluid, and
    ii. at least one lever in operative engagement with said at least one fluid tube;
  b. securing said at least one fluid tube and said at least one lever to the external surface of the electrosurgical device so that said at least one fluid tube second end is positioned proximate a working end of the electrosurgical device,
  wherein
    when said lever is in a first position, said lever prevents fluid from dispensing from said at least one fluid tube second end; and
    when said lever is in a second position, said lever moves out of engagement with said at least one fluid tube while engaging a power switch of the electrosurgical device.

18. The method of claim 17, wherein when said lever is in said second position, fluid is dispensed from said at least one fluid tube second end concurrently with energy activation of the electrosurgical device.

19. The method of claim 17, wherein
  a. said fluid delivery system further comprises a base that is configured to be removably attached to the electrosurgical device;
  b. said at least one fluid tube is operatively connected to said base; and
  c. said lever is operatively connected to said base and to the power switch.

20. The method of claim 17, further comprising the steps of providing a second fluid tube and securing said second fluid tube to the external surface of the electrosurgical device.

21. The method of claim 20, wherein said second fluid tube has a first end, a second end that is positioned proximate the electrosurgical device working end and a lumen that extends between said second fluid tube first and said second ends.

22. The method of claim 21, further comprising the steps of providing a second lever and securing said second lever to the external surface of the electrosurgical device so that said second lever is moveable between
  a. a first position in which said second lever engages said second fluid tube to close said lumen; and
  b. a second position in which said second lever moves out of engagement with said second fluid tube thereby allowing said second fluid tube lumen to open.

23. The method of claim 17, wherein said fluid delivery system is disposable.

* * * * *